United States Patent [19]
Inkpen et al.

[11] Patent Number: 6,025,727
[45] Date of Patent: Feb. 15, 2000

[54] DEVICE AND METHOD FOR DETECTING AND MEASURING FIBER PROPERTIES

[75] Inventors: Stuart Louis Inkpen, St. Phillips; Dana Charles Linfield, Portugal Cove; Christopher David Nolan, St. John's; John Charles Ebenezer Hall, St. John's; Christopher Hext Marshall, St. John's; Heather Lynn Spearns, St. John's, all of Canada

[73] Assignee: Instrumar Limited, St. John's, Canada

[21] Appl. No.: 09/196,193

[22] Filed: Nov. 20, 1998

Related U.S. Application Data

[63] Continuation-in-part of application No. 09/116,486, Jul. 16, 1998, which is a continuation-in-part of application No. 08/976,422, Nov. 21, 1997.

[51] Int. Cl.[7] .................................................. G01R 27/26
[52] U.S. Cl. ........................... 324/674; 324/663; 702/127
[58] Field of Search .................................... 324/713, 715, 324/707, 709, 686, 663, 674; 702/127

[56] References Cited

U.S. PATENT DOCUMENTS

| | | | |
|---|---|---|---|
| 4,084,434 | 4/1978 | Goodrich et al. ........................ 73/160 |
| 4,580,233 | 4/1986 | Parker et al. ........................... 364/550 |
| 4,706,014 | 11/1987 | Fabbri ....................................... 324/61 |
| 5,394,096 | 2/1995 | Meyer ..................................... 324/686 |
| 5,394,340 | 2/1995 | Inkpen et al. ........................... 364/550 |

FOREIGN PATENT DOCUMENTS

| | | |
|---|---|---|
| 1049114 | 2/1979 | Canada . |
| 1134039 | 10/1982 | Canada . |
| 2143272 | 8/1995 | Canada . |

*Primary Examiner*—Maura Regan
*Attorney, Agent, or Firm*—L. Anne Kinsman

[57] ABSTRACT

A device and method for measuring changes in denier, percent finish-on-yarn, interlacing of polymer fiber, and other fiber properties, in real time as the fiber is being manufactured. The device uses an electrode driven at a discrete voltage to induce a current which changes in amplitude and/or phase in response to changes in denier, finish-on-yarn and/or interlacing of a fiber. A sensing system samples the current and detects changes in the amplitude and/or phase. A computer, running an application program, quantifies the change and determines the applicable property.

18 Claims, 7 Drawing Sheets

DEVICE AND METHOD FOR DETECTING AND MEASURING FIBER PROPERTIES

This application is a continuation-in-part of U.S. patent application Ser. No. 09/116,486 filed Jul. 16, 1998, which is a continuation-in-part of U.S. patent application Ser. No. 08/976,422, filed Nov. 21, 1997.

FIELD OF THE INVENTION

This invention relates to a device and method for detecting and measuring the physical properties of fibers. In particular, this invention relates to a device and method for detecting and measuring fiber properties, such as denier, eveness, percent finish-on-yarn and the presence, distribution and physical properties of interlacing nodes of man-made and natural and both continuous and staple, fibers, substantially in real-time.

BACKGROUND OF THE INVENTION

In textile production, synthetic or man-made fibers are typically formed from a molten polymer material in a "spin-draw" process. The molten polymer, commonly nylon or polyester, is spun into filaments, five to five hundred of which are twined together to form a single fiber. The spun fiber is then drawn, altering the fiber's elasticity and tensile strength, and producing a continuous fiber with a desired final diameter. Natural fibers are typically spun from short lengths of natural material, such as wool or cotton, to form a staple fiber.

During the processing of the fiber, a "finish", typically a liquid emulsion, is applied to the fiber to lubricate its filaments and reduce static electricity buildup generated by the flow of the fiber through the processing machinery. Generally, the finish is water-based for nylons and oil-based for polyesters.

The industrial production of polymer fiber generally occurs at rates of 2,000 to 8,000 meters per minute, and can be as high as 6,000 meters per minute. Uniformity of the physical properties of the resulting fiber is critical to the performance and processing by the destined end user. Lack of fiber uniformity can result in costly production line shutdown, and/or product irregularities for end users, such as entanglement or breakage of the fiber during a weaving process and inconsistent fiber coloration.

During fiber production, several variables, such as temperature, roll surface, drawing speed, processing parameters and uneven application of the finish can affect the uniformity and properties of the fibers. Conventional measures of a fiber's properties are denier, the fiber density expressed as the weight in grams of a 9,000 meter length of fiber; and percent finish-on-yarn ("%FOY"), a measure of the amount of finish on the fiber; and interlacing. Interlacing nodes, also known as entanglement, are added to the fibers to provide a bond between the individual filaments that constitute each fiber. Generally, interlacing nodes are created regularly along the length of a fiber, typically every 5–20 cm, by exposing the fiber to a high velocity stream of air. Other fiber properties that are commonly measured include evenness, a measure of the variation of a fiber's denier, node distribution along the length of a fiber, and the size and formation of the nodes.

Currently, there is no reliable and cost-effective way to monitor the properties of fibers during production in real time as the fiber is being produced. As a result, fiber properties are measured after production. If the fiber properties fall outside accepted tolerances, substantial portions, or even whole runs, of production can be lost.

It is therefore preferable to determine fiber properties substantially in real-time as the fiber is being produced. Such a real time measurement system should be able to withstand shock, vibration, electromagnetic interference from equipment within a textile plant, and electrostatic charge build-up from contact with the passing fiber. The system should be generally insensitive to exposure to solvents used to clean the production line equipment, and splattering by finish as it is applied to the fiber.

In addition, if a real-time measurement system is to be adaptable to a variety of production environments, it should operate on a variety of fiber types. Further, as a fiber is composed of multiple filaments which can have different cross-sectional geometries, such as round, hollow, triangular and multi-lobed, the measurement system should also operate with a wide variety of fiber cross-sections.

Devices and analytical techniques exist for non-intrusive investigation of materials to deduce their physical properties. For example, dielectric sensors can measure the effects that the investigated material has on the capacitance of an imposed field. However, as is well known, such sensors exhibit problems with air gaps (U.S. Pat. No. 5,045,798, Hendrick and U.S. Pat. No. 5,095,278, Hendrick). Air gaps severely limit the sensors' ability to measure dielectric properties of a sample material as air and a vacuum have the lowest theoretically possible permittivity.

U.S. Pat. No. 4,706,014 to Fabbri and U.S. Pat. No. 5,394,096 to Meyer employ capacitive sensors to measure the diameter of a polymer fiber and denier, respectively. However, capacitive techniques can detect only relatively large variations in denier, can show extreme sensitivity to finish, and can be highly susceptible to fiber orientation and cross-section. Thus, such systems are not generally useful.

Electrostatic sensors are also known but also suffer from disadvantages in that they do not exhibit good sensitivity, are strongly affected by humidity and must be maintained at a specific distance from the material under investigation.

U.S. Pat. No. 5,394,340, which is owned by the assignee of the present invention and the contents of which are incorporated herein by reference, discloses a dielectric and capacitive sensor system for identifying and measuring substances, such as ice, on an aircraft wing. In this sensor system, sensor electrodes are driven to produce an electric field in a pattern which approximates a Bessel function. Current measurements are then taken from predetermined electrodes and analyzed to determine the nature and thickness of a layer of material overlying the sensor. While this sensor system is appropriate for identifying the presence or absence of layered materials on a surface, it is not capable of measuring the physical properties of a material moving at high speeds past the sensor.

SUMMARY OF THE INVENTION

It is an object of the present invention to provide a novel device and method for detecting and quantifying the physical properties of fibers and like materials substantially in real time which obviates or mitigates at least some of the disadvantages of the prior art.

In a first aspect of the present invention, there is provided a device for measuring at least one physical property of a fiber substantially in real time, comprising:

a driven electrode for placement adjacent a fiber of which at least one physical property is to be determined, said fiber moving relative to said driven electrode;

a control means to apply a voltage to said driven electrode means to induce a current in said driven electrode means, said induced current varying according to said at least one physical property;

a sensing means for sensing said induced current;

amplitude and phase detection means responsive to said sensing means for determining amplitude and phase of said sensed current at predetermined intervals;

analyzing means for analyzing said amplitude and phase to determine a measured value of said at least one physical property;

output means for outputting information representing said measured value.

In another aspect of the present invention, there is provided a method for detecting and quantifying at least one physical property of a fiber substantially in real time, said fiber moving relative to a driven electrode means, comprising the steps of:

(i) applying a voltage to said driven electrode means for inducing a current in said driven electrode means, said induced current varying according to said at least one physical property;

(ii) sensing said induced current;

(iii) determining amplitude and phase of said sensed current;

(iv) analyzing said amplitude and phase to determine a value for said at least one physical property; and (v) providing an output representing said value.

BRIEF DESCRIPTION OF THE DRAWINGS

Preferred embodiments of the present invention will now be described, by way of example only, with reference to the attached Figures, in which.

DETAILED DESCRIPTION

Figure 1:
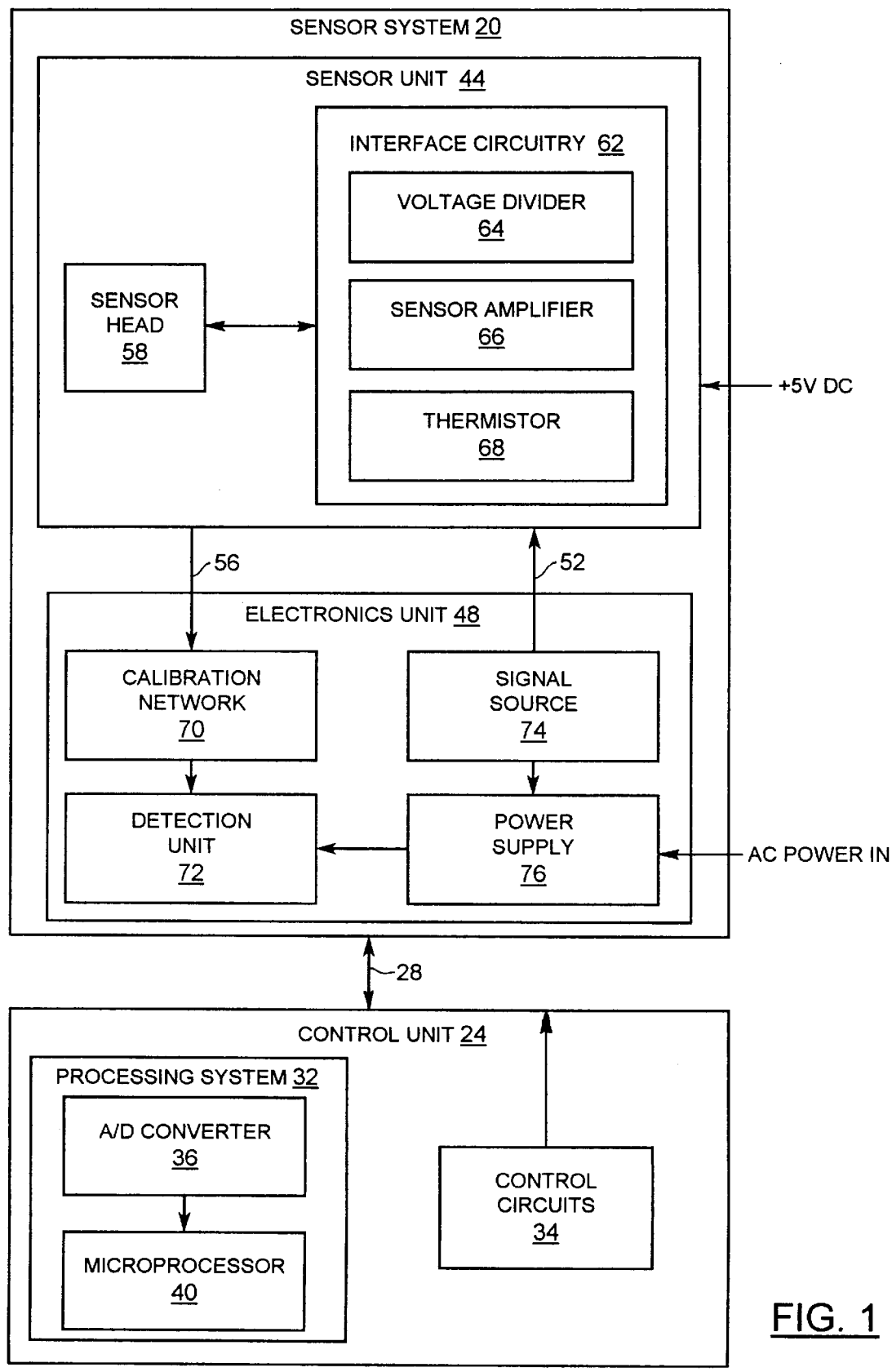
FIG. 1 shows a block diagram of a device for detecting and quantifying in accordance with the present invention.

A device 10 in accordance with an embodiment of the present invention is schematically illustrated in FIG. 1. Device 10 generally comprises a sensor system 20 connected to a control unit 24 through a communications system 28. Control unit 24 comprises a processing system 32 to acquire, convert and analyze data from the sensor system 20 and control circuitry 34 to control the operation of sensor system 20. Processing system 32 includes an A/D converter 36 and a microprocessor 40, such as an INTEL 80486, or better, and has a monitor for displaying results obtained with the device and other information.

Sensor system 20 consists of a sensor unit 44 and an electronics unit 48. Electronics unit 48 supplies excitation and control signals 52 to, and receives measurement signals 56 from, sensor unit 44. Sensor unit 44 includes a sensor head 58 and associated interface circuitry 62, including voltage drivers 64, a sense amplifier 66 and thermistor 68, which are responsive to the excitation and control signals 52 from electronics unit 48.

Electronics unit 48 generally comprises a calibration network 70, a detection unit 72, a signal source 74, and power supply 76. In a presently preferred embodiment, signal source 74 supplies a high frequency signal to drive sensor unit 44. As will be apparent to those of skill in the art, the optimal choice of this frequency depends upon the fiber and finish being measured. For example for common polymer fibers, the frequency will be in the range of from about 100 kHz to about 1 MHz, although frequencies outside this range may be employed for some materials.

Figure 1A:
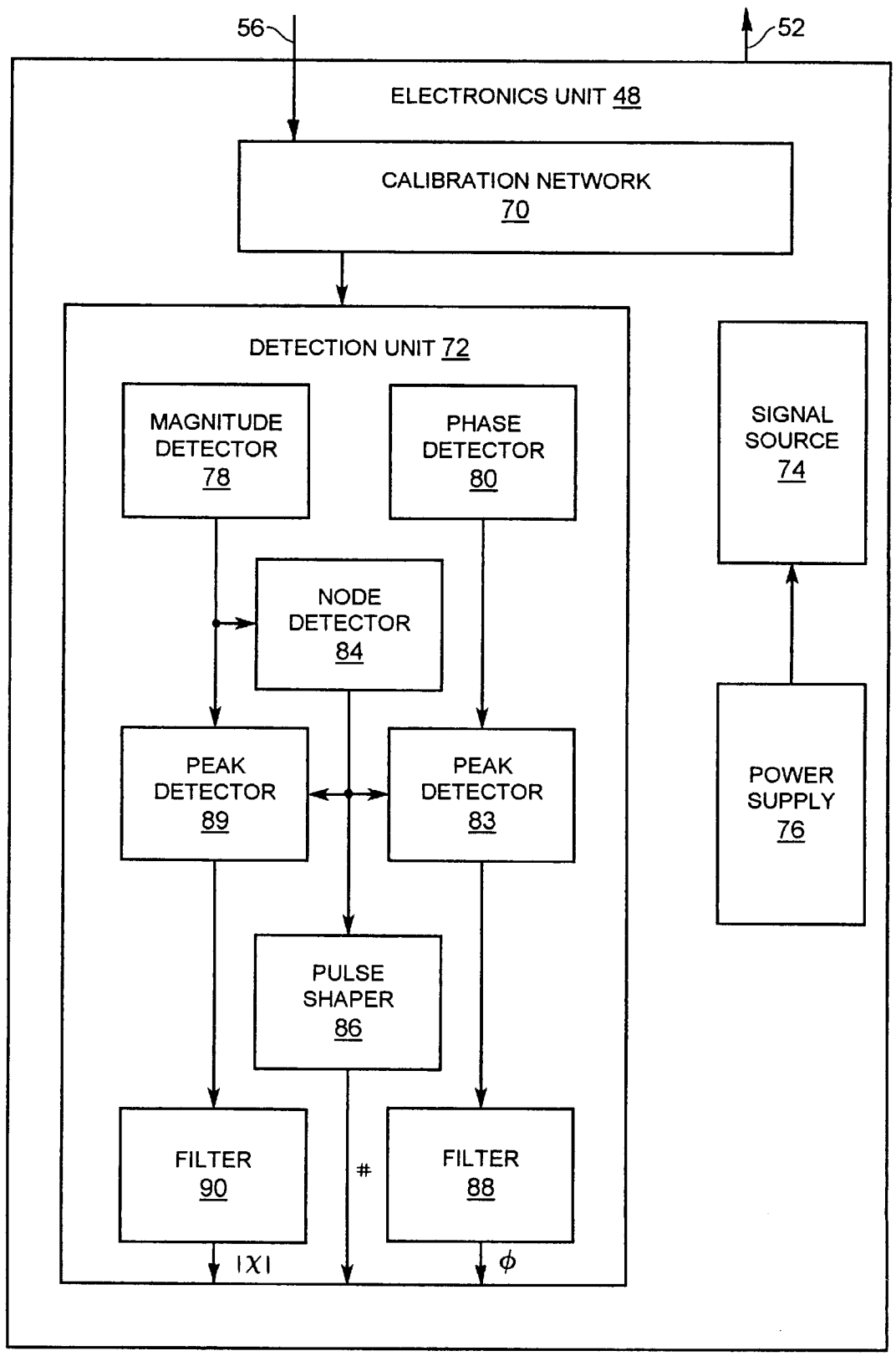
FIG. 1a shows a block diagram of the detection unit of the device of FIG. 1.

FIG. 1a shows an embodiment of electronics unit 48 in greater detail. In the illustrated embodiment, detection unit 72 includes a magnitude detector 78 and a phase detector 80, which receive signal 56 from calibration network 70, detect the magnitude and phase of the signal 56, respectively. A phase signal 81, representing the detected phase of signal 56 is the output of phase detector 80. Similarly, a magnitude signal 82, representing the detected magnitude of signal 56 is outputted from magnitude detector 78. Magnitude signal 82 is subsequently fed to a node presence detector 84 which detects the presence of interlacing nodes and outputs a presence signal 85 indicating the presence of a node, as will be more fully described below. Phase signal 81, magnitude signal 82, and presence signal 85, are then transmitted to processing system 32. Phase signal 81 passes to processing system 32 via a peak detector 83 and filter 88. Similarly, magnitude signal 82 passes to processing system 32 via a peak detector 89 and a filter 90. Presence signal 85 is transmitted to processing system 32 via a pulse shaper 86. Generally, the output from pulse shaper 86, and filters 88 and 90 represent the node position, phase and magnitude measurements of sensor system 20. A signal (not shown) from thermistor 68 can also be fed directly from the sensor unit 44 to the processing unit 32. In addition, general circuitry for filtering, scaling, amplifying and offsetting measurement signals 56 can also be integrated into detection unit 72. In a presently preferred embodiment, detection unit 72 operates upon analog signals 56, however, it is fully within the contemplation of the inventors that signals 56 can be digitized prior to input to electronics unit 48 and such prior digitization will not affect the general operation of device 10.

The design and construction of suitable electric circuits for interface circuitry 62 and electronics unit 48 is not particularly limited and can be any suitable configuration, as will occur to those of skill in the art.

Figure 2:
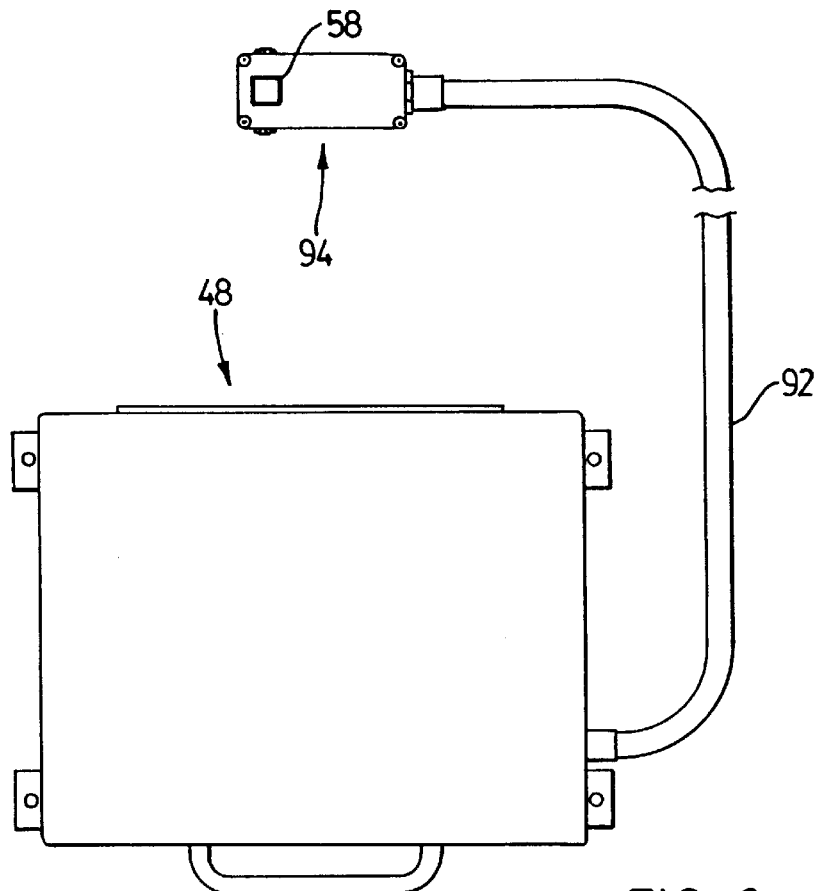
FIG. 2 shows a top view of a sensor system of the present invention.

Referring now to FIG. 2, a top view of an embodiment of sensor system 20 is illustrated. Sensor unit 44 is attached to electronics unit 48 by a conduit 92 through which run cables (not shown) carrying excitation and control signals 52 and measurement signals 56. In this configuration, sensor unit 44 is intended to be positioned on a fiber production line, such that sensor head 58 is in contact with a production run of fiber to be monitored. Electronics unit 48 can be fixed to the production machinery within a reasonable distance from the production line, in accordance with the length of conduit 92 provided. Sensor system 20 can generally be placed where appropriate relative to a production line, such that the fiber run, or a portion thereof, is in contact with system 20.

Figure 3:
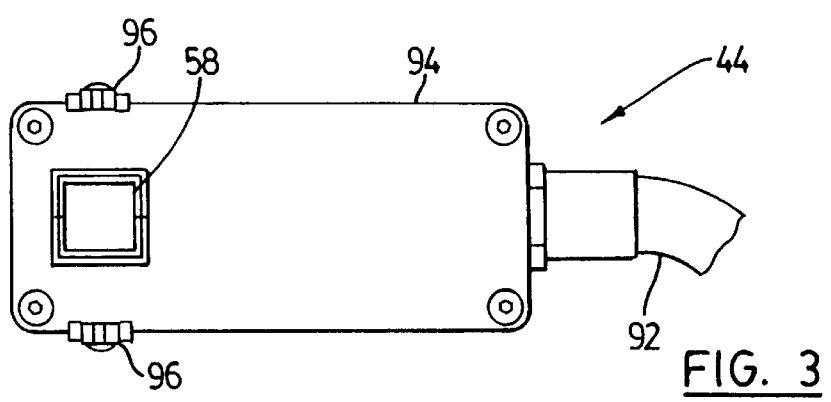
FIG. 3 shows a top view of a sensor unit of the present invention.
Figure 4:
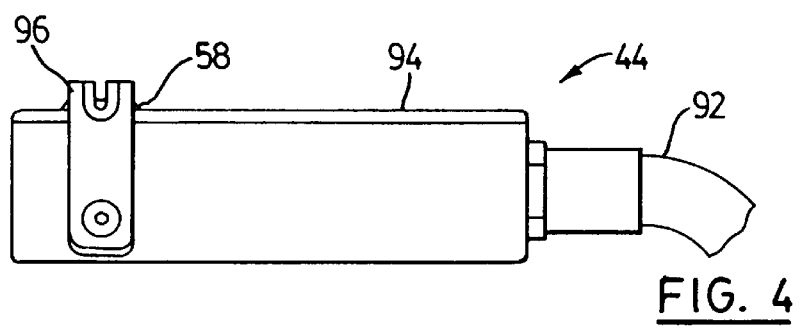
FIG. 4 shows a side view of the sensor unit of FIG. 3.

FIGS. 3 and 4 show the sensor unit 44 in greater detail. Sensor head 58, having a generally rectangular outline, is mounted on the upper face of a housing 94 to which is connected conduit 92. Fiber guides 96 are mounted on opposite sides of the housing 94, generally co-linear with the midpoint of the sensor head 58 and serve to guide a fiber being produced past sensor head 58, as discussed above. Guides 96 are formed of a suitable material, such as a ceramic material, to resist wear caused by movement of the fiber therethrough without damaging the fiber.

Figure 5:
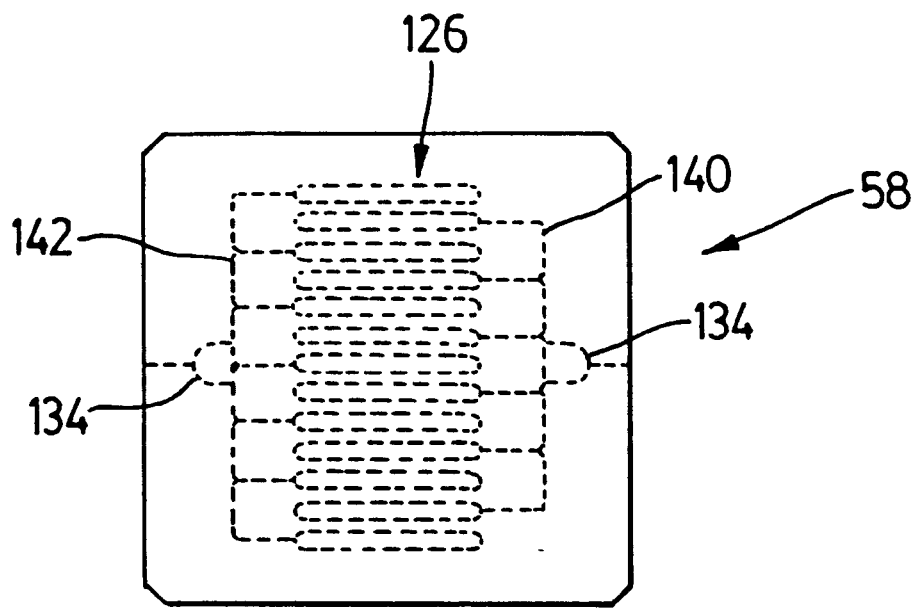
FIG. 5 shows a top view of a sensor head of the present invention.
Figure 6:
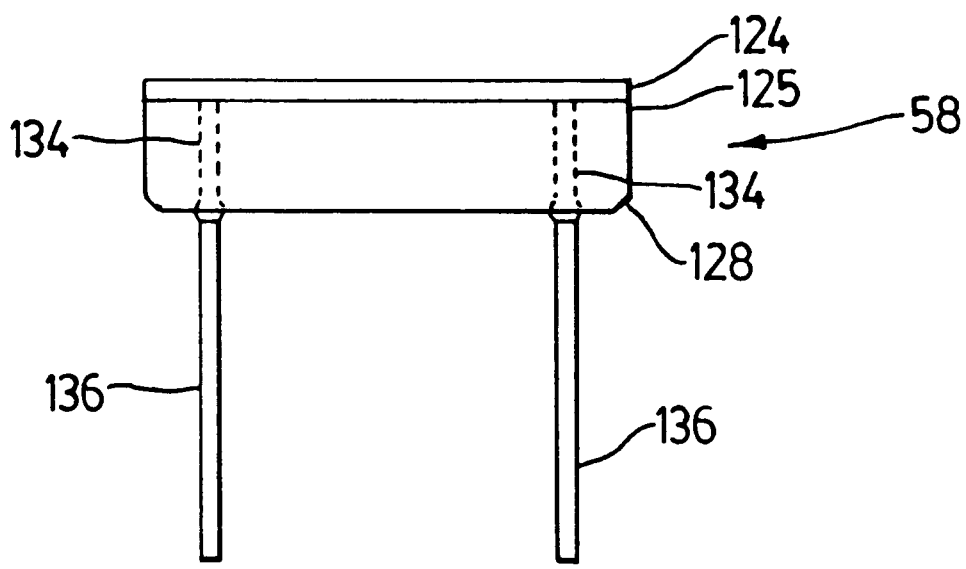
FIG. 6 shows a side view of the sensor head of FIG. 5.

Sensor head 58 is illustrated in more detail in FIGS. 5 and 6. The sensor head 58 has a protective layer 124 on its top surface. Immediately below the protective layer 124 is an electrode layer 125 having embedded therein electrodes 126. Below the electrode layer 125 is a backing layer 128. As will be understood by those of skill in the art, the materials chosen for protective layer 124 and backing layer 128 have appropriate electrical properties, such as permittivity and conductivity, and mechanical properties, such as resistance to erosion. The material selected should also be highly stable with temperature.

In one embodiment of the present invention, the present inventors have determined that fused quartz is an appropriate choice for both the protective layer 124 and backing layer 128. It has also been determined that MACOR™, a glass ceramic manufactured by Coming can also be used for the backing layer 128 where less abrasive conditions are experienced. In a preferred embodiment, electrode layer 125 is deposited on the upper surface of backing layer 128. Fused quartz is then sputtered on the backing layer 128 to form protective layer 124. The thickness of the protective layer 124 is chosen to provide sufficient abrasion protection to the electrode layer 125 while permitting sufficiently sensitive electrical interaction between the electrode layer 125 and a fiber running over top.

Generally, electrodes 126 are deposited onto backing layer 128 to form electrode layer 125. Two bores 134 extend through backing layer 128 and each bore 134 receives a connector pin 136 which electrically connects sensor head 58 to its associated interface circuitry 62. In the embodiment illustrated in FIG. 5, electrodes 126 are a set of parallel strip electrodes where alternate strips are interconnected to form two electrode patterns 140 and 142.

The number and geometry of the strip electrodes, and the distance separating each are governed by the maximum allowable size of the sensor, the desired electric field pattern, operating frequency, the required sensitivity and accuracy of the measurements. The selection, design and construction of the electrodes of sensor head 58 is within the normal skill of those of skill in the art and it will be apparent to those of skill in the art that electrode pattern geometries other than that illustrated in FIG. 5, can be used to measure denier, %FOY and the presence of interlacing nodes in fiber, evenness, node distribution, the physical attributes of the nodes, and other fiber properties that are a function of the output magnitude and phase signals.

Connector pins 136 extend through the bores 134 and are in electrical contact with the electrode patterns 140 and 142 and connector pins 136 are brazed or soldered to the back of the sensor head 58. As illustrated schematically in FIG. 1, sensor head 58 is electrically connected through connector pins 136 to interface circuit 62.

Figure 7:
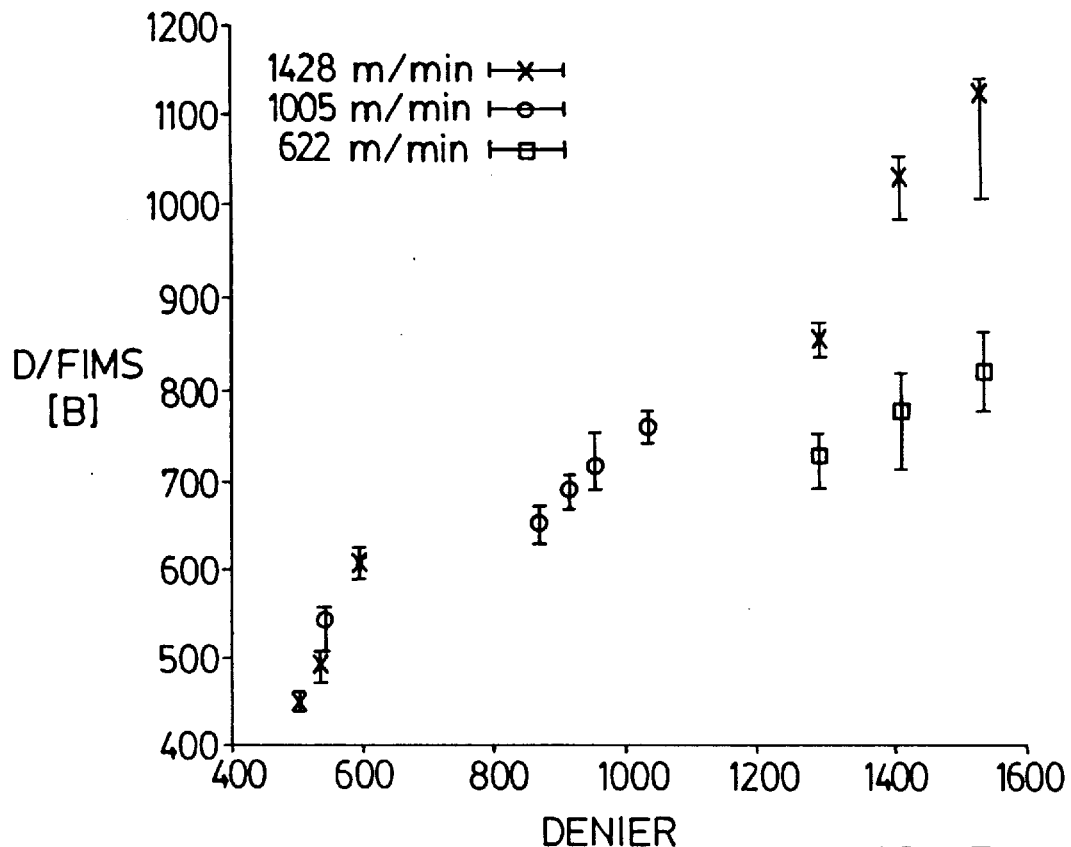
FIG. 7 shows a graphical representation of denier sensitivity for a device in accordance with an embodiment of the present invention.
Figure 8:
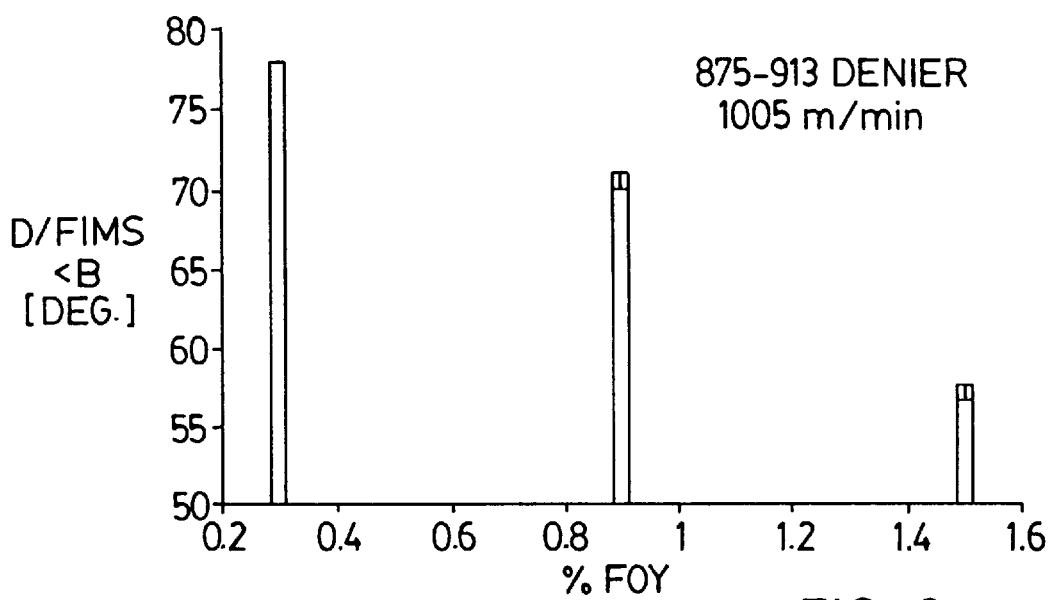
FIG. 8 shows a graphical representation of percent finish-on-yarn sensitivity for a device in accordance with an embodiment of the present invention.

The present inventors have determined that the fiber denier and %FOY can be measured as a functions of the detected magnitude and phase of a signal output by sensor system 20. In general terms, an increase in fiber denier corresponds to an increase in magnitude response and an increase in %FOY corresponds to a increase in phase response. FIG. 7 and FIG. 8 show typical sensitivities to changes in denier and %FOY, respectively, for a sensor device in accordance with the present invention. Absolute values for the denier and %FOY can be determined by comparing the peak measured amplitude and peak measured phase to previously correlated and calibrated values. Alternatively, a differential value can be calculated which indicates a deviation from a predetermined desired value. Evenness of a fiber, a function of the denier, can be calculated as well.

Figure 9:
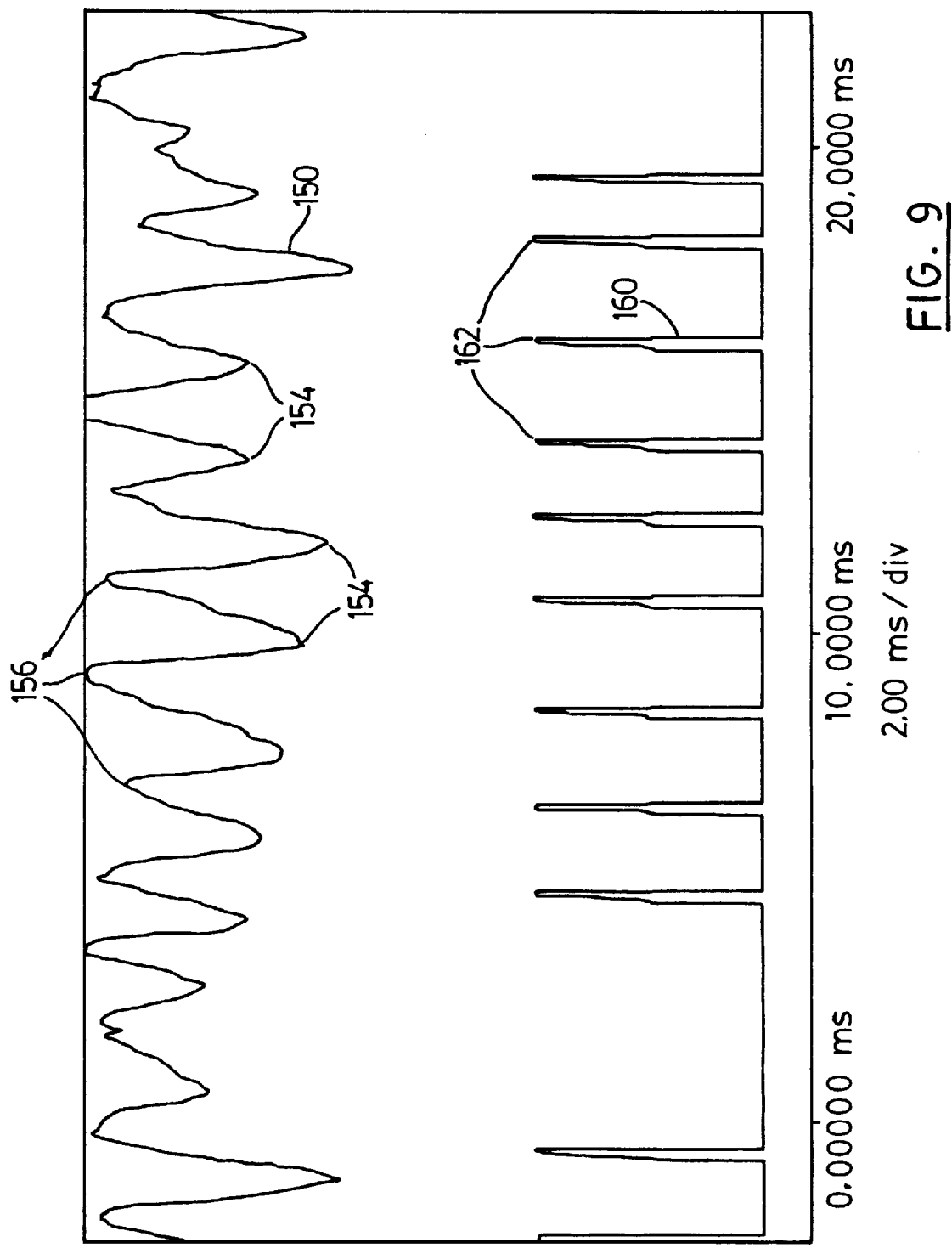
FIG. 9 shows a graphical representation of magnitude response in accordance with a further embodiment of the present invention.

The presence of interlacing nodes can be determined by analysing either the detected magnitude or phase. In a preferred embodiment, interlacing nodes are detected by analysing the magnitude signal 82 at node presence detector 84. Referring to FIG. 9, a typical waveform 150 depicting the detected magnitude response of sensor head 58 is shown. It has been found that null points 154 represent the presence of interlacing nodes on a fiber. Peak points 156 represent sections of nodeless fiber and, as described above, are a function of the denier of the fiber at a given point. Since each null point 154 represents the presence of an interlacing node, it is a simple operation to determine the number of nodes in a given length of fiber. The size of the magnitude response, the difference between the peak 156 and null 154 points can give a measurement of the size or intensity of each node. Similarly, the shape of the waveform 150 can be analyzed to provide a measurement of node intensity and strength. A flatter curve indicates poorly formed nodes, spread out along the fiber. A sharper curve indicates more discrete node formation.

The general operation of the illustrated embodiment of the present invention will be described with reference to the to FIGS. 1 and 1a. Electrode patterns 140 and 142 are driven one-hundred-and-eighty degrees out of phase, typically at a discrete frequency. Driving the two patterns 140 and 142 one-hundred-and-eighty degrees out of phase creates electric field patterns with low sensitivity to surrounding electrically grounded surfaces, such as housing 94 and the circuit board for electronics unit 48, thereby increasing the sensitivity of the device to physical properties of a fiber. The current in the electrode patterns 140 and 142, including both amplitude and phase, is passed from sensor head 58 to interface circuitry 62. Interface circuitry 62 relays the current signal, measurement signal 56, to calibration network 70 where it is calibrated as described below.

The calibrated measurement signal is then fed to the magnitude and phase detectors 78, 80 where the magnitude and phase, respectively, of the calibrated signal are determined and outputted as magnitude signal 82 and phase signal 81, respectively. The magnitude signal 82 is then fed to node presence detector 84. If no node is detected, the phase and magnitude signals 81 and 82 are passed by the peak detectors 83 an 89, filtered at filters 88 and 90, and fed to processing system 32. If an interlacing node is detected, a presence signal 85 is generated. The presence signal 85 triggers peak detectors 83 and 89 to take the peak values of the phase and magnitude signals, and to pass these peak values to the filters 83 and 89 and thence to the processing unit 32. The presence signal 85 is also fed to pulse shaper 86 the output of which is fed to processing unit 32 to produce a pulsed output 160, as shown in FIG. 9, each pulse 162 representing a node on the fiber. Analysis of the resulting output curves, such as those shown in FIGS. 7–9, is accomplished at microprocessor 40 in substantially real time, executing software that extracts the information relating to various fiber properties as previously described.

Figure 10:
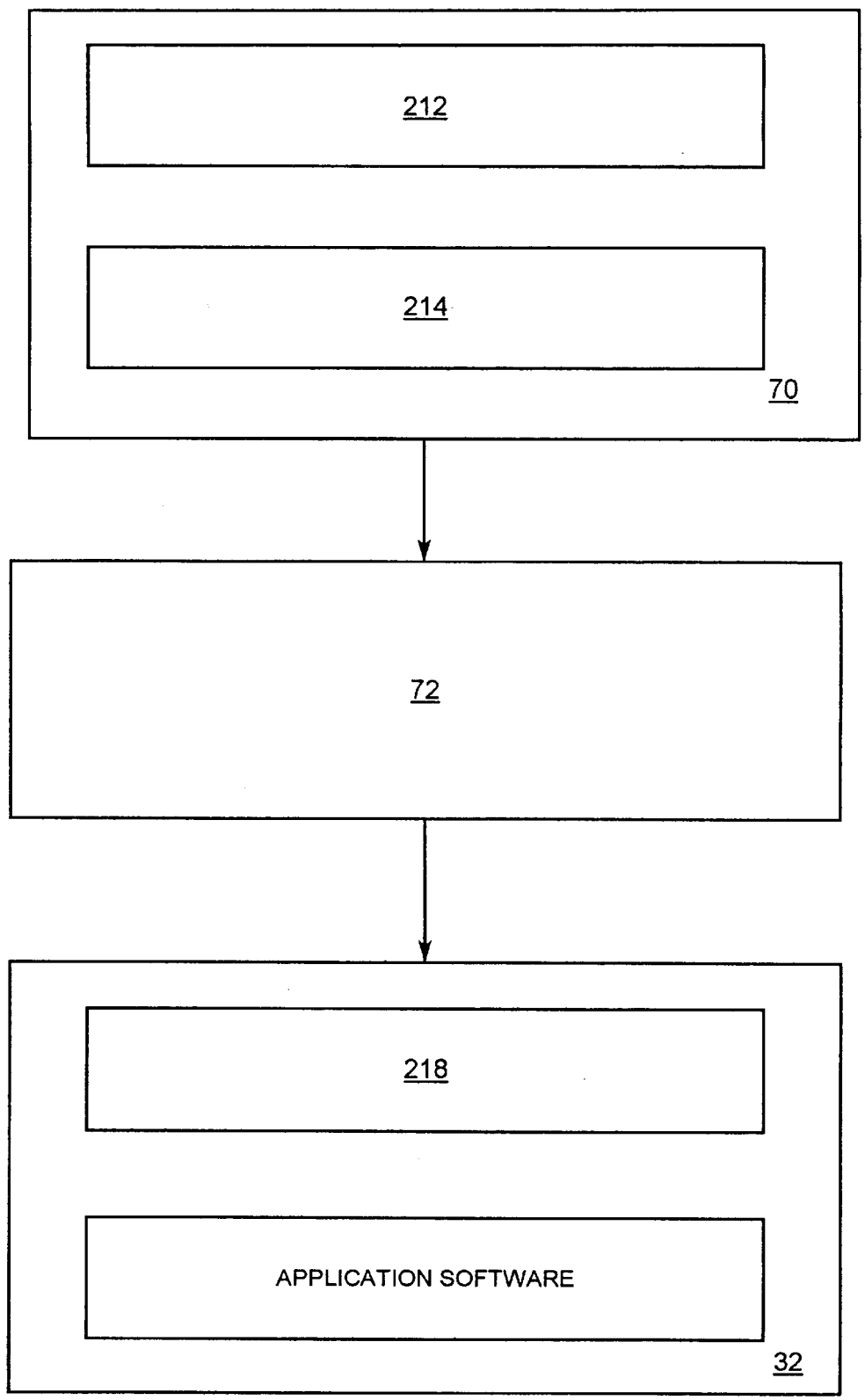
FIG. 10 shows a block representation of the measurement and calibration circuitry of an embodiment of the present invention.

In a further embodiment, device 10 operates upon a complex voltage ratio $V_I/V_O$ of two sinusoidal signals. $V_O$ is a measure of the voltage applied to the electrodes 126, and $V_I$ is a function of the output electrode current at the sense electrode 140. The ratio $V_I/V_O$ can be considered a measure of the admittance at the sensor head 58. The signals $V_I$ and $V_O$ are fed to calibration circuit 70, shown in block representation in FIG. 10. Included in the calibration network 70 is a precision reactive voltage divider 212 and a multiplexer 214 with three mode settings: (1) measure; (2) calibrate high; and (3) calibrate low. Voltage divider 212 and multiplexer 214 route signals $V_I$ and $V_O$ from the sensor interface circuit 62 (not shown) to phase and magnitude detectors 78, 80. Magnitude detector 78 includes two conventional magnitude detectors for determining the input and output dc voltage levels $M_I$ and $M_O$ of signals $V_I$ and $V_O$, and phase detector 80, determining phase P. The resulting outputs from peak detectors 83 and 89, a pulsed output 160 from pulse shaper 86, and a temperature measurement taken from thermistor 68 form a measurement set. Each measurement set is then transferred from the electronics unit 48, via the communications system 28, to the processing system 32, digitized at an A/D converter 32, and processed, typically using pre-programmed application software, to provide an absolute or differential measurement of denier and/or %FOY, and to determine the number of interlacing nodes present in the fiber.

Communications system 28 can be any suitable form of data transmission system. In the illustrated embodiment, the current from sensor head 58 is in an analog format and communications system 28 can either transmit this data in an analog format for conversion to a digital format at an interface to the processing system 32 or can convert this data into digital format prior to transmission to processing system 32. In the illustrated embodiment of the present invention, processing system 32 controls sensor system 20 to generate measurement sets at a sample rate of up to 100 Hz.

To precisely quantify the values in each measurement set, it is necessary to calibrate sensor system 20 to determine appropriate conversion parameters. In calibrate high and calibrate low modes, predetermined calibration signals equalling or exceeding the highest and lowest signals expected to be received by phase and magnitude detectors 78, 80 are routed from the voltage divider 212 to the detectors by the multiplexer 214. Assuming the calibration signals are constant, any changes in the gain of phase and magnitude detectors 78, 80 and offsets over time can be calibrated out. Further, by measuring and storing, actual voltage levels and relative phase at the inputs of phase and magnitude detectors 78, 80 for the calibrate high and calibrate low modes, variation of the gains and offsets of phase and magnitude detectors 78, 80 can be calibrated out.

By comparing the resulting dc output levels of phase and magnitude detectors 78 in the calibrate high and calibrate low modes to stored voltage and phase readings, the calibration readings can be used to translate the dc output levels of phase and magnitude detectors 78, 80 for the input voltage magnitude, output voltage magnitude and phase into corresponding voltage magnitude levels $|V_I|$ and $|V_O|$, and relative phase $\Phi$ in degrees. By dividing the two magnitudes a calibrated vector voltage ratio $[|V_I/V_O|, \Phi]$ is obtained, where $V_I/V_O$ is essentially a measure of admittance.

In the present embodiment of the invention, an offset equivalent to the reading of the sensor with just air, no fiber, is subtracted from the reading to improve the dynamic range of the reading. The effective drive level is sensed through a buffer as $V_O$. Also connected to the electrode 140 can be two admittances $Y_L$ and $Y_H$ used for the low and high calibrations, respectively. $Y_L$ and $Y_H$ can be switched in place of the admittance of the sensor head 58, $Y_X$, for calibration of the sensor readings. $Y_L$ and $Y_H$ are selected to exceed the minimum and maximum expected admittance range by approximately 20%. Calibration measurements of the outputs with admittances $Y_L$ and $Y_H$ permits calibrating out any non-linear effects in the interface circuit 62, and relates subsequent measurements to $Y_L$ and $Y_H$. Also, offset admittances YOF1 and optional $Y_{OF2}$ can be connected to improve the dynamic range of response.

An accurate determination of the admittance $Y_T$ of the fiber passing over sensor head 30 can then be determined from the equation:

$$\frac{V_I}{V_O} = \frac{Y_{FI} + 2*Y_T + Y_S - 0.5*Y_{OFI}}{Y_{FI}} = G*Y_T + N$$

where:
$Y_{F1}$ is the first stage circuit feedback admittance;
$Y_T$ is the admittance to be measured;
$Y_S$ is unwanted stray coupling admittance;
$Y_{OF1}$ is the first stage offset correction admittance;
G is the gain of the sense amplifier; and
N is the offset To determine the denier and %FOY of the fiber passing over sensor head 58, an interpretation algorithm is required to analyze the magnitude and phase measurements. The numerical analysis currently contemplated by the present inventors uses two equations to estimate fiber denier and %FOY as a function of the magnitude and phase measurements as follows:

$$D(M,P) = a_1 + b_1 M + c_1 M^2 + d_1 P + e_1 P^2$$

$$F(M,P) = a_2 b_2 P/M + c_2 P^2$$

where:
D is the estimated fiber denier;
F is the estimated %FOY;
M is the magnitude measurement;
P is the phase measurement;
$b_1, c_1, d_1, e_1, b_2, c_2$ are fixed scaling coefficients; and
$a_1, a_2$ are scaling offsets that are determined periodically during sensor calibration.

As will be apparent, the sensor device of the present invention is subject to a certain degree of electrical noise. Noise effects can be lessened by any suitable technique, as will occur to those of skill in the art. Internal sources of noise can include data time smearing, ground loop noise, case sensitivity, cross talk, sense amplifier transient response and sense amplifier zero response. External sources of noise can include electromagnetic interference from variable motors within a textile plant, and electrostatic charge build-up from the charged fibers.

It will be apparent to those skilled in the art that the foregoing is by way of example only. Modifications, variations and alterations may be made to the described embodiments without departing from the scope of the invention which is defined solely in the claims.

We claim:

1. A device for monitoring multiple physical properties, substantially in real time, of a fiber as it is manufactured, comprising:

a sensor head having a first electrode pattern and a second electrode pattern, for placement adjacent a fiber of which multiple physical properties are to be determined as the fiber moves relative to the sensor head at industrial production speeds;

a signal source for applying a high frequency signal to the sensor head to induce electric fields of opposite phase in the first and second electrode patterns the fields varying in response to changes in the multiple physical properties as the fiber passes the sensor head;

a detection unit for sampling the fields at predetermined intervals, and for determining current magnitude, current phase, and voltage values thereof;

a processing unit for analyzing the magnitude, phase and voltage values to extract measurements of the multiple physical properties in substantially real time; and output means for outputting information representing the measurements.

2. A device according to claim 1, wherein said fiber is a polymer fiber.

3. A device according to claim 1, wherein the physical properties include denier.

4. A device according to claim 1, wherein the physical properties include percent finish-on-yarn.

5. A device according to claim 1, including peak detection means, responsive to at least one of said determined magnitude and phase, for determining a peak response.

6. A device according to claim 5, wherein the physical properties include interlacing.

7. A device according to claim 5, wherein the physical properties include node distribution.

8. A device according to claim 1, wherein the physical properties include eveness.

9. A method for monitoring multiple physical properties of a fiber during manufacture, substantially in real time, comprising the steps of:

(i) applying a high frequency signal to a sensor head to induce electric fields, having opposite phases, in first and second electrode patterns of the sensor head, the fields varying in response to changes in the physical properties as the fiber passes the sensor head at industrial production speeds;

(ii) sampling the fields at predetermined intervals;

(iii) determining current magnitude, current phase and voltage values of the sampled fields;

(iv) analyzing the magnitude, phase and voltage values to determine measurements of the multiple physical properties in substantially real time; and (v) providing an output representing said measurements.

10. A method according to claim 9, wherein said fiber is a polymer fiber.

11. A method according to claim 9, wherein said physical properties include denier.

12. A method according to claim 9, wherein said physical properties include percent finish-on-yarn.

13. A method according to claim 9, including a step after step (iii) of determining a peak response of at least one of said determined magnitude and phase.

14. A method according to claim 13 wherein said at least one physical property is interlacing.

15. A method according to claim 13, wherein said physical properties include node distribution.

16. A method according to claim 9, wherein said physical properties include evenness.

17. A device according to claim 1, wherein the fiber is moving at a speed in the range of 2,000 to 8,000 m/min.

18. A method according to claim 9, wherein the fiber is moving at a speed in the range of 2,000 to 8,000 m/min.

* * * * *